(12) United States Patent
Behramand

(10) Patent No.: US 12,404,483 B2
(45) Date of Patent: Sep. 2, 2025

(54) SYSTEM AND METHOD FOR GROWING ALGAE

(71) Applicant: Simak Behramand, Irvine, CA (US)

(72) Inventor: Simak Behramand, Irvine, CA (US)

( * ) Notice: Subject to any disclaimer, the term of this patent is extended or adjusted under 35 U.S.C. 154(b) by 571 days.

(21) Appl. No.: 17/845,511

(22) Filed: Sep. 12, 2022

(65) Prior Publication Data
US 2024/0084232 A1    Mar. 14, 2024

(51) Int. Cl.
  *C12M 3/06*   (2006.01)
  *C12M 1/00*   (2006.01)
  *C12M 1/12*   (2006.01)
  *C12M 3/00*   (2006.01)
  *C12N 1/12*   (2006.01)

(52) U.S. Cl.
  CPC .............. *C12M 21/02* (2013.01); *C12M 3/06* (2013.01); *C12M 23/04* (2013.01); *C12M 23/48* (2013.01); *C12M 29/04* (2013.01); *C12M 31/02* (2013.01); *C12N 1/12* (2013.01)

(58) Field of Classification Search
  CPC ........ C12M 21/02; C12M 3/06; C12M 23/04; C12M 23/48; C12M 29/04; C12M 31/02; C12N 1/12
  USPC ...................................................... 489/289.1
  See application file for complete search history.

*Primary Examiner* — Bobby Ramdhanie
(74) *Attorney, Agent, or Firm* — Trojan Law Offices

(57) ABSTRACT

System and method for growing and harvesting algae. A plurality of growing trays containing growing medium for growing algae are arranged for flow of the growing medium sequentially therethrough. A holding tray configured to hold more growing medium than any one of the plurality of growing trays receives the growing medium from the plurality of growing trays. A pump draws the growing medium from the holding tray back into the plurality of growing trays.

14 Claims, 3 Drawing Sheets

SYSTEM AND METHOD FOR GROWING ALGAE

TECHNICAL FIELD

The disclosure relates generally to bioreactors, and more particularly to systems and methods of cultivating algae for harvesting.

BACKGROUND

Algae has many potential uses. Some types of microalgae have very high levels of digestible protein, which makes them appropriate as food sources. Some types are considered good candidates for renewable biodiesel because of their high concentration of lipids. Algae has also been used for purifying and recycling wastewater, as well as in the pharmaceutical industry. As such, there has been some interest in developing bioreactors for algae. To date, greater adoption of algae has been hampered by cost and reliability issues.

Culturing microalgae is difficult because it typically requires large water surface areas and a well-controlled environment with respect to lighting and supply of nutrients and gases (oxygen and carbon dioxide). For example, vertical bioreactor assemblies with lighting (photobioreactors) and built-in gas permeable membranes to regulate gas supply have been proposed as efficient alternatives, as in U.S. Pat. No. 8,713,850 B2. Other proposed approaches include using open ponds, vertically suspended polyethylene sleeves, aquarium systems, raceway (open pools), glass tubes or vertical alveolar panels, horizontally oriented panels configured to maximize sunlight exposure (flat plate reactors or FPRs), and outdoor cultivation using the air-lift method. For example, in several of these approaches, it is thought that productivity is increased by increasing surface area to volume ratio of the nutrient-rich water container where the algae is being cultured.

Nutrient quantity and quality, light, pH, turbulence, salinity, and temperature are important factors determining growth of algae. For example, preferably for good growth, with respect to the underlying growing (culture) medium, the temperature may be between 16-27° C. or 18-24° C., the salinity may be between 12-40 g/l or 20-24 g/l, the light intensity (lux) may be between 1,000-10,000 lux, and the pH may be between 7-9 or 8.2-8.7. A variety of micronutrients may be required, e.g. various trace metals, thiamin (Vitamin B1), cyanocobalamin (Vitamin B12) and biotin. Several growing media have been suggested in the literature, e.g. the Walne medium and Guillard's F/2 medium. Various fertilizers may be used, e.g. Ammonium sulfate, urea, and calcium superphosphate. Aeration and mixing may be necessary to avoid thermal stratification and to ensure every part of the algae population is exposed to light and nutrients. However, certain microalgae may be sensitive to aggressive mixing.

In practice, it is found that achieving reliable and predictable cultivation (production) is difficult as microalgae may be unusually sensitive to variations and perturbations in operating parameters and the environment. Low yields may considerably increase costs. The low cell density of microalgae and the high cost of source material makes the need to achieve high yields more important. During operation, reliability and robustness of an algae bioreactor may be important. For example, a production facility may undergo power loss or surge, especially if it is powered by renewable energy such as solar power. In such cases, it is important to mitigate catastrophic loss of algae cultures and allow effective restart of operations at low cost.

SUMMARY

Removal of carbon from the atmosphere is recognized as important for addressing climate change. Plants and other vegetation are significant sinks for carbon, since they consume carbon dioxide during photosynthesis. Algae, in particular, can play an important role because of their fast maturation and their high rate of photosynthesis, particularly in photobioreactors. Cost-efficient and scalable photobioreactors are needed to address the climate crisis.

Costs associated with building and operating algae growing systems (e.g. photobioreactors) are significant, and need to be reduced to improve economic competitiveness of carbon removal via algae cultivation. Algae feedstock itself may be very expensive. Algae may be relatively sensitive to environmental and operating conditions, which increases costs and imposes difficulties for individuals or small entities that want to cultivate algae. Costs may be reduced by improving yields, making yields predictable, increasing reliability and robustness of algae growing systems, and reducing use of primary resources such as land.

Algae growing systems are known to be prone to catastrophic failure, e.g. if there is a loss of power, which may increase costs. In many cases, to maintain environmental effectiveness or due to remote locations of facilities, algae growing systems are operated using renewable electricity that may be interrupted from time to time.

In one aspect, the disclosure describes a system for growing algae, comprising: a plurality of growing trays, each of the plurality of growing trays containing growing medium for growing algae, the plurality of growing trays arranged for flow of the growing medium sequentially through the plurality of growing trays; a holding tray receiving the growing medium from the plurality of growing trays, the holding tray configured to hold more growing medium than any one of the plurality of growing trays; and a pump drawing the growing medium from the holding tray into the plurality of growing trays.

In another aspect, the disclosure describes a method of growing and harvesting algae, comprising: causing gravity-induced flow of algae-laden growing medium sequentially through a plurality of growing trays configured to cultivate algae; receiving the algae-laden growing medium from the plurality of growing trays in a holding tray extending horizontally below each of the plurality of growing trays, the holding tray configured to receive spillage of the growing medium from the plurality of growing trays; extracting algae from the algae-laden growing medium in the holding tray for harvesting while retaining algae in the algae-laden growing medium to allow cultivation to continue; and supplying the algae-laden growing medium from the holding tray to the plurality of growing trays to continue to cultivate algae.

Embodiments can include combinations of the above features.

The sensitivity and yield of algae may be improved by using larger growing trays. e.g. at least 17 cm or at least 20 cm in vertical depth, and the holding tray, which encourages mixing and homogenization (reduction of gradients, including thermal gradients). Placing the holding tray below the growing trays, and dimensioning the holding tray to be larger than the growing trays, prevents catastrophic failure in case of spillage, allows open-air cultivation, and reduces the need for coverings. Using a growing tray-based system may facilitate scalability.

It is found that algae yields (production) can be improved by reducing stress on algae, particularly for algae such as blue-green algae and other hard-to-cultivate microalgae. Larger growing trays and the holding tray may reduce algal stress. The growing medium flows from one growing tray to another and to the holding tray due to gravity. The growing trays are inclined with respect to the horizontal to cause gravity induced flow. The (slope) grade is controlled to be between 0.5-3% or substantially 2%. This generates a waterfall effect that increases aeration and reduces algal stress, without forcing overflow or jet-like ejection of growing medium from growing trays.

Algae is harvested, via filtration, from the holding tray. This avoids stressing the algae in the growing trays and reduces gradients in algal concentration when filtered growing medium is returned to the system, since it is returned to the mixing environment of the holding tray. Harvesting retains a portion of the algae in the holding tray so that algae may be recirculated back into the growing trays for culturation, obviating or considerably reducing the need to procure new algae feedstock during operation.

Sensors for measuring salinity (via electrical conductivity), light intensity, turbidity, pH, and temperature, are used to monitor the algae growing system. A user or operator may be notified, via a user terminal, if measured values are outside one or more acceptable values. For example, mitigation actions may be taken in case of a power loss or other scenario generating a risk of system failure. In such a manner, robustness and reliability of the system may be improved.

In some embodiments, algae produced in systems may generate oxygen more efficiently than trees. The amount of oxygen produced in a few hours may be comparable to that of several trees in at least a year's time. Additionally, land requirements are considerably reduced in embodiments compared to land requirements for planting trees with similar oxygen generation (or carbon dioxide absorption) capacities.

In some cases, water evaporation may be reduced as well.

Further details of these and other aspects of the subject matter of this application will be apparent from the detailed description included below and the drawings.

DESCRIPTION OF THE DRAWINGS

Reference is now made to the accompanying drawings, in which.

DETAILED DESCRIPTION

Figure 1B:
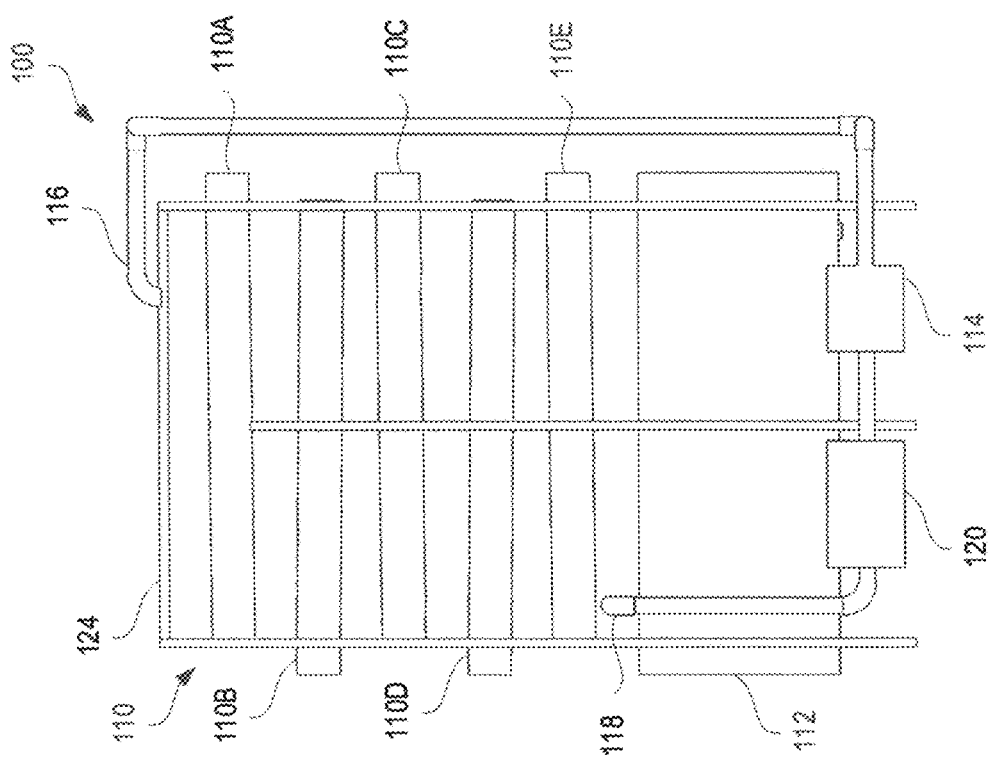
FIG. 1B is a side view of the system of FIG. 1A.

The following disclosure relates to bioreactors for algae. In some embodiments, compared to prior art assemblies, the systems and methods disclosed herein may facilitate higher yields of algae during production, with greater reliability, smaller physical footprint, and with reduced risk of catastrophic loss of algae cultures.

Systems and methods disclosed herein may involve culturing (or cultivating) algae in a plurality of vertically spaced apart growing trays that are arranged in sequence (vertically "daisy-chained" or multilevel) and which contain a (flowable) algae-laden growing medium, e.g. nutrient-rich water. The growing trays may be uncovered and open to the atmosphere to facilitate gas exchange and may be inclined with respect to the horizontal to generate (relatively gentle) gravity-induced flow of the growing medium from a highest growing tray to a lowest growing tray, from where the growing medium drains into a holding tray. The multi-level structure may help achieve scalability.

The holding tray may extend horizontally below all the growing trays to provide catchment for spills and overflow from the growing trays, e.g. in case of system failure. Harvesting of algae may be carried out from the holding tray, e.g. by passing growing medium (laden with algae) through a filtering device. It is found that, under gravity without additional forcing, more mature algae tends to more readily accompany growing media flowing out of the growing trays, which then improves the quality of algae obtained from harvesting the holding tray and ensures the growing trays have a relatively greater proportion of young algae. Only a portion of algae may be extracted from the holding tray to maintain growing medium therein ready for further cultivation, thereby reducing the need to top-up the growing trays with exogenously produced algae culture, which may be costly. A pump may recycle the growing medium from the holding tray back into the highest growing tray to continue cultivation of algae.

In various embodiments, the system may be adapted to reduce stress on algae, which may boost production. In various embodiments, the system may be configured to reduce sensitivity to physically localized or generally small variations and perturbations, e.g. by encouraging physical and chemical homogenization of the growing medium, which may improve reliability. In various embodiments, the system may be adapted to mitigate catastrophic loss of algae, e.g. by providing larger growing trays and an even larger holding tray that all reduce the chance of immediate failure if power is lost.

It is conceived that the embodiments may be used in a variety of applications.

Growing algae at home may not only be an alternate source of income for many households but may also incentivise adoption of emission reduction approaches and technologies. For example, homes may each become an air purifier and an algae production plant.

In polluting industries, or in sections of cities where carbon dioxide emissions are higher, aspects disclosed herein may be used to absorb carbon dioxide and turn it into oxygen in a simple and inexpensive manner. This may lead to improved air quality and reduction of greenhouse gases.

Algae cultivated in accordance with some embodiments may be used in food production, as embodiments may be used to generate algae with protein as well as good fats and sugars. Food production may include human food and animal feed, including aquatic animals.

Algae cultivated in accordance with some embodiments may be used to generate biodiesel and fertilizer, as well as in the pharmaceutical industry.

Algae cultivation may be used for air and wastewater treatment.

Aspects of various embodiments are now described in relation to the figures.

Figure 1A:
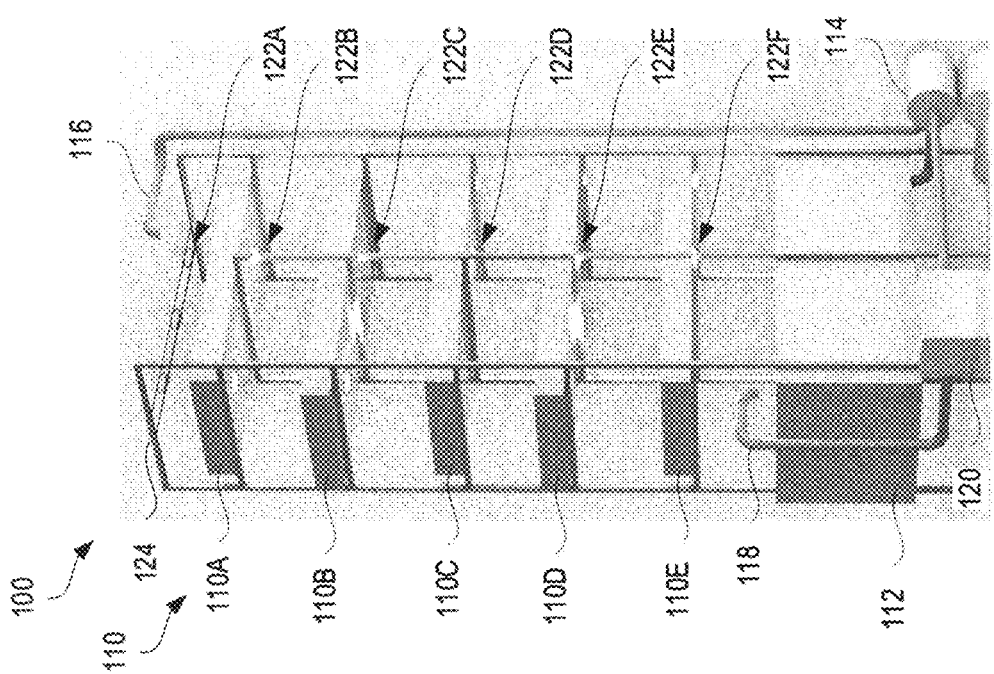
FIG. 1A is a perspective view of a system for growing algae, in accordance with an embodiment.

FIG. 1A is a perspective view of a system 100 for growing algae, in accordance with an embodiment.

FIG. 1B is a side view of the system 100 of FIG. 1A.

The system may include growing trays 110A, 110B, 110C, 110D, 110E, collectively referred to as (a plurality of) growing trays 110. Each growing tray 110A, 110B, 110C, 110D, 110E may contain growing medium for growing algae.

As referred to herein, the growing medium may be a flowable (in terms of rheological properties) medium adapted for culturing of algae, e.g. nutrient-rich water or other liquid having dissolved oxygen. The algae itself may be suspended in the growing medium, e.g. microalgae may be suspended therein. As such, unless indicated otherwise, references to growing medium are meant to include microalgae that may be suspended therein. In various embodiments, algae may include blue-green algae contained in the growing medium.

The growing trays 110 may be open trays. One or more ends or faces of each of the growing trays 110 may be exposed to the atmosphere to facilitate gas exchange and for receiving light. In various embodiments, the growing trays 110 may be constructed from rigid or structural material, e.g. stiff plastics and/or metals.

The growing trays 110 may be arranged for flow of the growing medium sequentially through the growing trays 110. The growing medium may flow from growing tray 110A to growing tray 110B, from growing tray 110B to growing tray 110C, from growing tray 110C to growing tray 110D, and from growing tray 110D to growing tray 110E. Following this, a holding tray 112 (or holding tank) may receive the growing medium from the plurality of growing trays 110 via the growing tray 110E.

The growing trays 110 may be horizontally inclined and offset from one another both vertically and horizontally. Vertical spacing allows gravity-induced flow while horizontal spacing defines respective spillways adjacent to the growing trays 110 where growing medium may flow into an adjacent lower one of the growing trays 110. Such a positioning of the growing trays 110 may achieve cultivation of algae by facilitating extraction of atmospheric carbon dioxide by the algae by encouraging the growing medium to flow in a zig-zag manner from the growing tray 110A to the growing tray 110E (and to the holding tray 112).

Gravity-induced flow achieved by inclined growing trays 110 is found to reduce stress on the algae, e.g. by reducing shear. It is found that mature algae, and algae in higher concentrations, may more readily accompany growing media flowing out of the growing trays 110; the gravity-induced flow may preferentially select for more mature algae. Microalgae may generally comprise five consecutive phases of culturation: initial lag or induction phase, exponential growth phase, phase of declining relative growth, stationary growth phase, and death phase. Harvesting mature algae in the stationary growth phase or death phase ensures a high rate of growth of algae, and thus increases carbon capture from the environment.

A pump 114 may be configured to draw the growing medium from the holding tray 112 into the plurality of growing trays 110 via a conduit 116. The conduit 116 may supply the growing medium to the growing tray 110A.

A filtering device 120 may be fluidly connected to the holding tray 112 to receive the growing medium, laden with algae, therefrom. The filtering device 120 may harvest algae by filtering algae from this algae-laden growing medium and then supply algae-depleted growing medium back to the holding tray 112 via a conduit 118. In some embodiments, the filtering device 120 may be a filter press.

In various embodiments, the pump 114 may be used to pump growing medium in the holding tray 112 into the filtering device 120. In some embodiments, this may be accomplished by a (actuatable) valve disposed between the pump 114 and the holding tray 112. In some embodiments, the valve may have a first position and a second position: in the first position, the pump 114 may be connected to the conduit 116 to pump the growing medium vertically up to the growing tray 110A, and in the second position, the pump 114 may be connected to the filtering device 120 to pump growing medium thereinto. In some embodiments, the valve may have a third position or may be a flow divider valve, such that the pump 114 simultaneously supplies both the filtering device 120 and the growing tray 110A. In some embodiments, the valve may include an assembly of faucets.

In various embodiments, the pump 114 may be a positive-displacement pump or a piston pump.

In various embodiments, the filtering device 120 and the pump 114 may work substantially continuously. Continuous filtering may prevent excess algae build-up in the holding tray 112 and the in the growing trays 110. In case of interruption of power, the growing trays 110 may gradually drain into the holding tray 112. The relatively greater holding volume of the holding tray 112 and the exposure thereof to the atmosphere (for gas exchange) may prevent catastrophic failure and allow the algae to continue cultivation for a period of time.

The holding tray 112 may be dimensionally larger, or at least as large, as any one of the growing trays 110. The holding tray 112 may be positioned below all of the growing trays 110 so that any spillage, intended or not, may be caught by the holding tray 112. For example, if there is a power surge and increased growing medium is provided to the growing trays 110 by the pump 114 via the conduit 116, excess growing medium may spill into the holding tray 112. In various embodiments, the holding tray 112 may be sufficiently large (with respect to volume) to hold growing medium spilling from all the growing trays 110.

Lighting fixtures 122A, 122B, 122C, 122D, 122E important for growth may provide artificial lighting to the respective growing trays 110A, 110B, 110C, 110D, 110E. Lighting fixture 122F may provide artificial lighting to the holding tray 112. For example, LED or SMD lights may be installed.

In various embodiments, parts of the system 100, including the growing trays 110, the holding tray 112, and the lighting fixtures 122A, 122B, 122C, 122D, 122E, 122F may all be mounted onto a frame 124.

In some embodiments, the system 100 may be portable or moveable. For example, the system 100 may have wheels attached to the frame 124 below the holding tray 112 to facilitate relocation and movement of the system 100.

In some embodiments, the frame 124 may be composed of metal (such as aluminum or steel) and structurally capable of handling the weight of the growing trays 110, the holding tray 112, and other components. In various embodiments, the frame 124 may be painted with anti-rust paint. The frame 124 may have a plurality of vertical columns. In various embodiments, at least four vertical columns may be provided. Depending on the weight, number, length and width of the growing trays 110 (volume and weight), the number of vertical columns may be increased. The frame 124 may have a plurality of horizontal shafts for supporting the growing trays 110. The horizontal shafts may hold the growing trays 110 horizontally. In various embodiments, the number of horizontal shafts may be equal to the number of growing trays 110. In various embodiments, the frame 124 may include a ladder to facilitate an operator overseeing the structure.

In some embodiments, the growing trays 110 may be situated on each level of the frame 124 with little gap from one another. The bottom of a growing tray may be configured to provide light to a lower level growing tray.

In some embodiments, the growing trays 110 may be cuboid with a vertical depth of substantially 17 cm and horizontal dimensions of 188 cm by 81 cm. In some embodiments, inter-growing tray spacing may vary between 17 cm and 19 cm. For example, the inter-growing tray spacing may be larger at one end of the growing tray compared to the other end, depending on the slope (since it induces additional spacing).

In some embodiments, the holding tray 112 may be cuboid with a vertical depth of substantially 80 cm and horizontal dimensions of 199 cm (which is greater than the 188 cm dimension of the growing tray) by 103 cm (which is greater than the 81 cm dimension of the growing tray). In various embodiments, the vertical depth of the holding tray 112 may be substantially greater than the number of growing trays 110 multiplied by the vertical depth of a growing tray.

Figure 2:
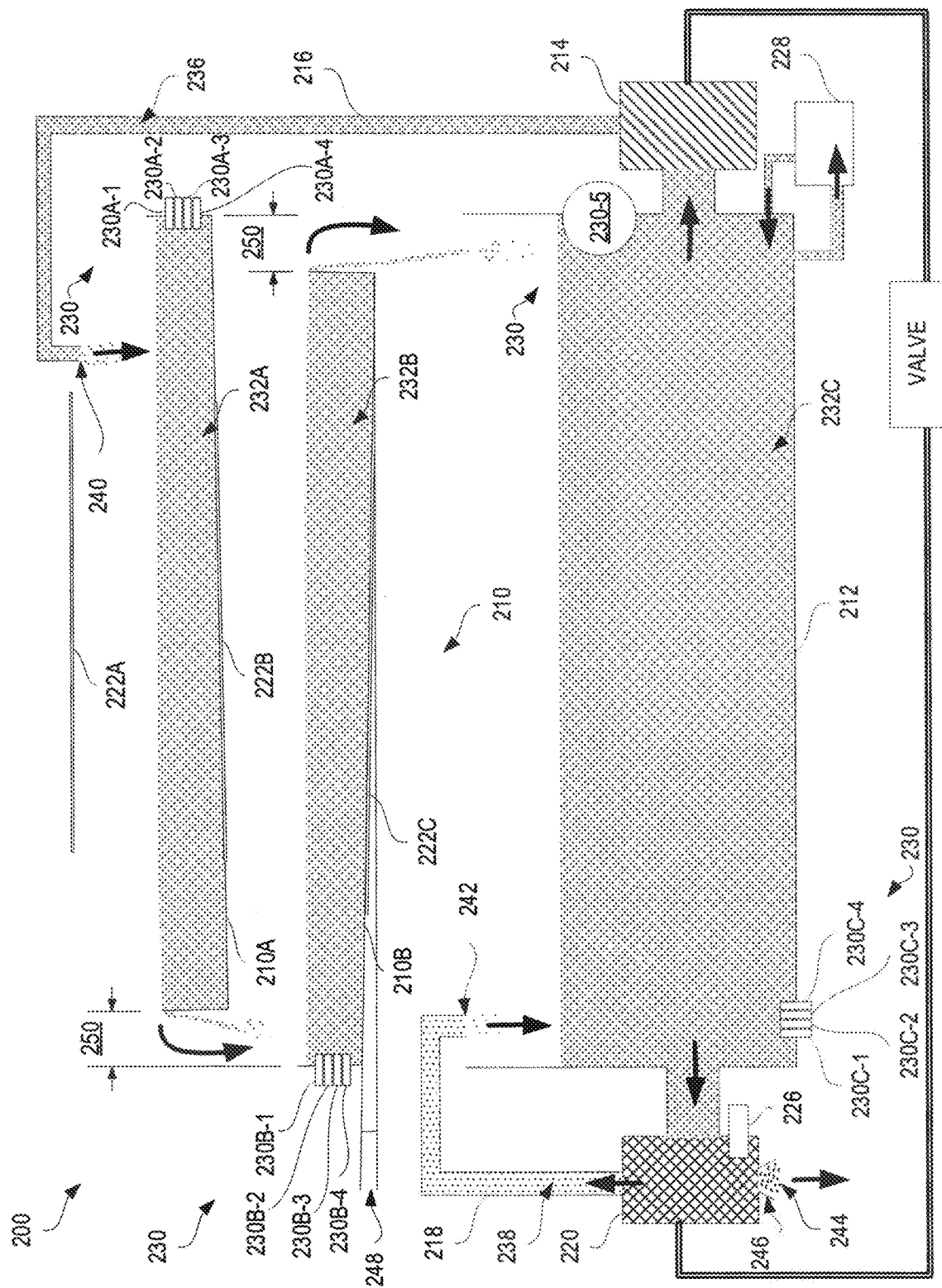
FIG. 2 is a schematic cross-sectional view of a system for growing algae, in accordance with an embodiment.

FIG. 2 is a schematic cross-sectional view of a system 200 for growing algae, in accordance with an embodiment. Material flow, e.g. of growing medium and algae, is generally indicated with thick black arrows.

The system 200 may have growing trays 210A, 210B, collectively referred to as growing trays 210, containing growing medium 232A, 232B. The growing trays 210 drain into a holding tray 212 containing growing medium 232C. The growing trays 210 may be vertically spaced apart from each other to cause gravity-induced flow of the growing medium.

The growing trays 210 may each be inclined with an inclination slope 248 (with respect to the horizontal) to direct the flow of the growing medium sequentially through the plurality of growing trays 210. In various embodiments, the grade or inclination slope 248 may vary between 0.5% and than 3% (100×tangent of the inclination angle or rise over run). In some embodiments, the inclination slope 248 is substantially 2%. For example, flow velocity and shear may increase with a greater inclination slope 248. It is found that inclination slopes above 3% may stress the algae, reduce aeration, and reduce yields. Lower inclination slopes may generate a waterfall effect and may encourage water to slide down while covering the entire edge or face of the growing tray to increase aeration. However, excessively small slopes may lead to low flow and/or overflow or spillage (from the sides, e.g.).

The growing trays 210 may be horizontally spaced apart, misaligned, or staggered to define spillways 250 adjacent to the lower portions of each of the (inclined) growing trays 210. Gravity-induced flow may occur sequentially through the growing trays 210 and into the holding tray 212, and preferentially via the spillways 250.

The growing trays 210 may be configured to cultivate algae, e.g. they may include lighting sources, nutrient supply, and may be shaped to encourage culturing of algae. In various embodiments, each of the growing trays 210 may extend vertically (have a vertical depth of) at least 20 cm, 17 cm, or between 17 cm and 25 cm. For example, certain types of algae may provide better yields with a larger depth. It is found that lower depths make the algae sensitive and prone to failure.

The growing trays 210 may be disposed above the holding tray 212. The holding tray 210 may extend horizontally below each of the plurality of growing trays 210 to receive spillage of the growing medium from the plurality of growing trays 210. For example, the horizontal dimensions (such as length, width, or diameter) of the holding tray 212 may be sufficiently large or larger than corresponding dimensions of the growing trays 210. To handle spillage volumes, the holding tray 212 may be configured to hold volumetrically more growing medium than the plurality of growing trays 210 or any one of the plurality of growing trays 210. In various embodiments, the holding tray 212 may not be inclined itself.

The system 200 may comprise water-level or liquid-level regulators or regulating pins, which may be used to regulate the growing medium's surface level in the growing trays 210, and to keep the surface levels level. In some embodiments, such regulators may include aquarium water-level regulators or floating regulators. In various embodiments, all the growing trays 210 have substantially the same level of growing medium for quality control.

In various embodiments, the growing trays 210 may be constructed of polyethylene, light concrete, galvanized metal, plexiglass and/or other similar materials.

Lighting fixtures 222A, 222B, 222C may be disposed over, respectively, growing trays 210A, 210B, and the holding tray 212 to encourage growth of algae in the corresponding growing media 232A, 232B, 232C.

A pump 214 draws growing medium 232C from the holding tray 212 into the growing tray 210A via a conduit 216. Algae-laden growing medium 236 flows through the conduit 216 and is deposited into the (top-most) growing tray 210A via an opening 240 of the conduit 216. The pump 214 may be operated using electricity or another power source.

In various embodiments, nutrients (such as nitrogen and phosphate) and other amendments (such as alkali) or supplements may be added to the growing trays 210A, 210A and/or the holding tray 212 to facilitate cultivation of algae. In some cases, such materials may be supplied to the growing trays 210A, 210B indirectly via the holding tray 212. In various embodiments, a dedicated feeder may be provided in the growing trays 210A, 210A and/or the holding tray 212 to facilitate adding nutrients and other additives.

A filtering device 220, fluidly connected to the holding tray 212, may be used to remove algae from the holding tray 212 for harvesting. In some embodiments, the filtering device 220 may be a filtering press. Algae 244 filtered in the filtering device 220 may be ejected from the system 200 via an outlet 246. The residual growing medium is returned back to the holding tray as algae-depleted growing medium 238 via a conduit 218 having an outlet 242 opening to the holding tray 212.

In various embodiments, the filtering device 220 may be configured to remove about 70% of algae, by weight, from a growing medium received thereinto. In some embodiments, no more than 80% and no less than 20%, by weight, of algae in the algae-laden growing medium may be extracted by the filtering device 220 for harvesting. Leaving residual algae in the growing medium may reduce costs of filtering and may also facilitate recycling the algae for providing seed material that may then culture/grow in the holding tray 212 and the growing trays 210.

In some embodiments, the filtering device 220 may be coupled to a sanitization system 226 to sanitize the algae 244 prior to ejection from the outlet 246. In some embodiments, the sanitization system 226 may effectively sanitize the algae-depleted growing medium 238 before it is returned to the holding tray 212. For example, a need for injecting fresh water into the system 200 may be thereby reduced.

In various embodiments, the sanitization system 226 may be used to remove contaminants and may include ultraviolet irradiation and/or exposure to ozone. In some embodiments, ozone may be optional. In some embodiments, exposure to LED lighting may be sufficient, e.g. in carbon removal applications. For example, contaminants may include dust. Sanitization may eliminate bacteria, protozoa, or competing species of algae, all of which may be problematic for certain types of microalgae.

In some embodiments, a condenser 228 or other cooling device may be fluidly connected to the holding tray 212 for cooling the growing medium 232C. In this way, the temperature of the growing media in the holding tray 212, as well as the growing trays 210 may be controlled.

In some embodiments, a gas bubbler or pump may be provided, e.g. to provide a means of carbon dioxide and/or oxygen entry, e.g. in case of deficiencies, for control, or as backup during shutdowns or unexpected failures.

The system 200 may include one or more sensors 230 to facilitate maintaining appropriate conditions for algae growth. For example, the sensors may be configured to measure at least one of electrical conductivity, pH, light sensor, turbidity, or temperature.

In some embodiments, one or more of the growing trays 210A, 210B or the holding tray 212 may have respective electrical conductivity (EC) sensors 230A-1, 230B-1, 230C-1. EC sensors 230A-1, 230B-1, 230C-1 may be configured to measure EC of the growing medium and may provide a measure of salinity, e.g. to detect whether the salinity falls outside an acceptable range. In some embodiments, acceptable ranges include 12-40 g/l or 20-24 g/l. In various embodiments, if the salinity falls outside the acceptable range, salinity may be increased by supplying additional saline or decreased by replacing a portion of the growing medium with a lower salinity solution (or injecting non-saline liquid such as fresh water), once the sensor detects the salinity.

In some embodiments, one or more of the growing trays 210A, 210B or the holding tray 212 may have respective pH sensors 230A-2, 230B-2, 230C-2. pH sensors 230A-2, 230B-2, 230C-2 may be configured to measure pH of the growing medium, e.g. to detect whether the pH falls outside an acceptable range. In some embodiments, acceptable ranges include 7-9 or 8.2-8.7. In various embodiments, if the pH falls outside the acceptable range, alkaline or acid may be injected to adjust the pH to within the desired range. In some cases, it is found that air contamination may gradually increase acidity, unless remedied.

In some embodiments, one or more of the growing trays 210A, 210B or the holding tray 212 may have respective light sensors 230A-3, 230B-3, 230C-3. Light sensors 230A-3, 230B-3, 230C-3 may be configured to measure the quantity and quality of incident light in the growing medium, e.g. to detect whether the light intensity falls outside an acceptable range. In some embodiments, acceptable ranges include 1,000-10,000 lux or 2,500-5,000 lux. In various embodiments, if the light intensity falls outside the acceptable range, it may be an indication of failure of a light fixture. As such, additional lighting may be provided in compensation once the sensor detects the loss of light.

In some embodiments, one or more of the growing trays 210A, 210B or the holding tray 212 may have respective temperature sensors 230A-4, 230B-4, 230C-4. Temperature sensors 230A-4, 230B-4, 230C-4 may be configured to measure the temperature of the growing medium, e.g. to detect whether the temperature falls outside an acceptable range. In some embodiments, acceptable ranges include 16-27° C. or 18-24° C. In various embodiments, if the temperature falls outside the acceptable range, heating and/or cooling devices, such as the condenser 228, may be used to adjust the temperature of the growing medium to within the acceptable range. For example, the temperature sensors 230A-4, 230B-4, 230C-4 may function as thermostats.

In various embodiments, the holding tray 212 may have a turbidity sensor 230-5. Higher turbidity may be an indication of greater concentration of algae. Thus, the turbidity sensor 230-5 may be used to infer algae concentration, and thus also maturity (since, without injection of new algae, increased concentration is achieved with algae growth and reproduction over time).

Sensors 230 may include, or may refer to one or more of, sensors 230A-1, 230B-1, 230C-1, 230A-2, 230B-2, 230C-2, 230A-3, 230B-3, 230C-3, 230A-4, 230B-4, 230C-4, 230-5.

In some embodiments, only the holding tray 212 may have one or more sensors 230, e.g. to reduce costs and improve efficiency associated with sensor equipment and processing of sensor data, as described earlier. Recycling growing medium from the holding tray 212 to the growing trays 210 may allow efficient sensing of an overall status of the system 200 and algae growing conditions. In various embodiments, sensors 230 in the holding tray 212 may provide an indication (e.g. as a proxy) of conditions in the growing trays 210. In various embodiments, control of conditions in the growing trays 210 may be controlled by varying conditions in the holding tray 212.

During operation to grow and harvest algae, the system 200 may circulate growing medium through the growing trays 210A, 210B and holding tray 212 substantially continuously or intermittently. The circulation is achieved by the operation of the pump 214 which lifts growing medium from the holding tray 212 to the growing tray 210A. In some embodiments, algae-laden growing medium from the holding tray 212 is drawn into the plurality of growing trays 210 while maintaining, volumetrically, at least as much algae-laden growing medium in the holding tray 212 as in any one of the plurality of growing trays 210.

As the algae-laden growing medium flows vertically downwards after injection into the growing tray 210A via the outlet 240, culturing of algae may substantially continually generate mature algae. The amount of algae in the growing trays 210 may generally increase from the top-most to the bottom-most growing tray. For example, the growing medium 232B in growing tray 210B may be laden with more algae than the growing medium 232A in the growing tray 210A. The amount of algae in the holding tray 212 may generally tend to increase, as the concentration of algae in the growing medium 232C increases due to deposition from the growing trays 210A, 210B. Algae may then be extracted from the algae-laden growing medium in the holding tray 212 for harvesting while retaining sufficient algae therein to allow cultivation to continue or not be substantially disrupted. The residual algae is supplied in the form of algae-laden growing medium from the holding tray 212 to the plurality of growing trays 210.

In some embodiments, the relatively large depth of the holding tray 212 in comparison to the growing trays 210 may encourage mixing (homogenization) and aeration without introducing additional shear, which could damage the algae. In some cases, reliability, robustness, and yield may be increased.

Example Operation

The pump is run for about 30 minutes to supply growing medium to the growing trays 210A, 210B and the holding tray 212. Once the liquid surface levels in each growing tray rise to the top therein, physical and chemical parameters, such as pH and EC levels, are measured and regulated. The initial cultivation of the algae (inoculum value), prepared at a lab, is added to the holding tray 212. Lighting fixtures 222A, 222B, 222C are then activated, at which time initial cultivation at all levels starts leading to production of algae. During cultivation/production, an operator may check the physical, chemical and biological parameters in a timely manner and, if need be, makes adjustments to such parameters to achieve high-quality, reliable growth.

Once the turbidity (of growing medium) in the holding tray 212 reaches the desired level (as measured by the turbidity sensor 230-5), algae growth is at its maturity and can be effectively harvested. At such time, a valve connected to the pump 214 changes position. The pump 214 transfers the growing medium containing the algae to the filtering device 120, e.g. a filter press where the algae is trapped in ten folded filter compartments. The filtered growing medium is then returned to the holding tray 212.

Turbidity of the growing medium in the holding tray 212 may drop due to harvesting of algae. When the turbidity of the water reaches a low threshold level, the valve may change position to cut off supply of growing medium to the filtering device 220. The system 200 may then restart growing/cultivating algae, where the trapped or residual algae in growing medium in the system 200 then plays the role of the initial cultivation (inoculum value). The operator by, adjusting physical and chemical conditions and injecting feed supply into the system, then may facilitate restarting of algae reproduction. The filtering device 120 may be emptied, e.g. a filtering press may be emptied since algae by way of specialized partitions in the filter press may be separated from the filter. Filters of the filtering device 220 may be washed and returned back to the filtering device 220. The process may then be repeated.

Figure 3:
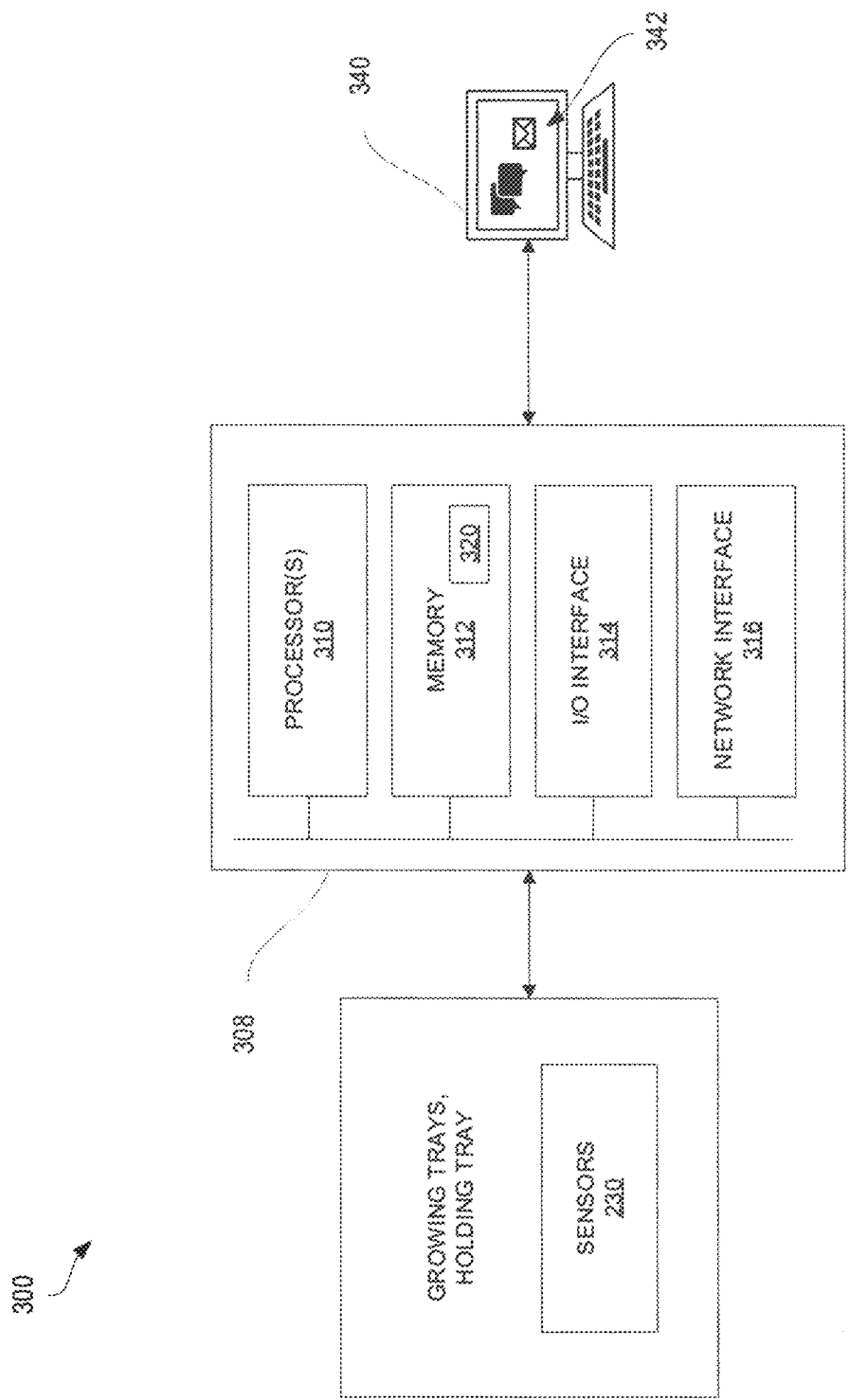
FIG. 3 is a schematic block diagram of a system for growing algae including a user terminal for providing a notification to a user, in accordance with an embodiment.

FIG. 3 is a schematic block diagram of a system 300 for growing algae including a user terminal 340 for providing a notification 342 to a user, in accordance with an embodiment.

Sensors 230 installed on growing trays and holding trays, as described earlier, may communicate with a machine 308, e.g. a computing device or a server, comprising one or more processors 310, and machine-readable memory 312. In some embodiments, the machine 308 may have an input/output interface 314 and a network interface 316.

The processors 310 may be configured to execute machine-readable instructions 320 stored on the machine-readable memory 312.

The instructions 320, when executed by the processors 310, cause the system 300 to perform steps including: receiving one or more sensor values from the sensors 230, and transmitting a notification 342 to a user terminal 340 when the sensor value falls outside a predetermined range. A user or an operator may decide to take action with respect to the algae growing system 200 based on the notification 342.

Examples of the user terminal 340 include a computer with a GUI, a smartphone device, a speaker configured to send messages to an operator, and/or a paging device.

As can be understood, the examples described above and illustrated are intended to be exemplary only.

The embodiments described in this document provide non-limiting examples of possible implementations of the present technology. Upon review of the present disclosure, a person of ordinary skill in the art will recognize that changes may be made to the embodiments described herein without departing from the scope of the present technology. For example, the growing trays may be arranged at least partially sequentially in a horizontal direction, and growing trays and the hold tray may be cylindrical or in the form of another non-cuboid shape. Yet further modifications could be implemented by a person of ordinary skill in the art in view of the present disclosure, which modifications would be within the scope of the present technology.

The term "connected" or "coupled to" may include both direct coupling (in which two elements that are coupled to each other contact each other) and indirect coupling (in which at least one additional element is located between the two elements).

Although the embodiments have been described in detail, it should be understood that various changes, substitutions and alterations can be made herein without departing from the scope. Moreover, the scope of the present application is not intended to be limited to the particular embodiments of any processes, machines, manufactures, compositions of matter, means, methods and steps described in the specification.

As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized. Accordingly, the embodiments are intended to include within their scope such processes, machines, manufacture, compositions of matter, means, methods, or steps.

What is claimed is:

1. A system for growing algae, comprising:
   a plurality of growing trays, each of the plurality of growing trays containing growing medium for growing algae, the plurality of growing trays arranged for flow of the growing medium sequentially through the plurality of growing trays;
   a holding tray receiving the growing medium from the plurality of growing trays, the holding tray configured to hold more growing medium than any one of the plurality of growing trays; and
   a pump drawing the growing medium from the holding tray into the plurality of growing trays.

2. The system of claim 1, wherein the holding tray is configured to hold volumetrically more growing medium than the plurality of growing trays.

3. The system of claim 1, wherein growing trays of the plurality of growing trays are vertically spaced apart from each other and above the holding tray to cause gravity-induced flow of the growing medium sequentially through the plurality of growing trays and into the holding tray, and the holding tray extends horizontally below each of the plurality of growing trays to receive spillage of the growing medium from the plurality of growing trays.

4. The system of claim 3, wherein the each of the plurality of growing trays is inclined between 0.5% and 3% to direct the flow of the growing medium sequentially through the plurality of growing trays.

5. The system of claim 1, further comprising:
   a filtering device fluidly connected to the holding tray to harvest algae by filtering algae from algae-laden growing medium, the filtering device configured to receive the algae-laden growing medium from the holding tray and to supply algae-depleted growing medium back to the holding tray, the holding tray holding sufficient algae to continue cultivation of algae.

6. The system of claim 1, wherein each of the plurality of growing trays extends vertically between 17 cm and 25 cm.

7. The system of claim 1, further comprising:
a condenser fluidly connected to the holding tray for cooling the growing medium.

8. The system of claim 1, wherein the growing medium contains blue-green algae for growing.

9. The system of claim 1, further comprising:
a sensor configured to measure at least one of electrical conductivity, pH, light sensor, or temperature;
a machine-readable memory; and
a processor configured to execute machine-readable instructions stored on the machine-readable memory, which, when executed by the processor, cause the system to perform steps including:
receiving a sensor value from the sensor, and
transmitting a notification to a user terminal when the sensor value falls outside a predetermined range.

10. A method of growing and harvesting algae, comprising:
causing gravity-induced flow of algae-laden growing medium sequentially through a plurality of growing trays configured to cultivate algae;
receiving the algae-laden growing medium from the plurality of growing trays in a holding tray extending horizontally below each of the plurality of growing trays, the holding tray configured to receive spillage of the growing medium from the plurality of growing trays;
extracting algae from the algae-laden growing medium in the holding tray for harvesting while retaining algae in the algae-laden growing medium to allow cultivation to continue; and
supplying the algae-laden growing medium from the holding tray to the plurality of growing trays to continue to cultivate algae.

11. The method of claim 10, wherein the algae-laden growing medium from the holding tray is drawn into the plurality of growing trays while maintaining, volumetrically, at least as much algae-laden growing medium in the holding tray as in any one of the plurality of growing trays.

12. The method of claim 10, wherein no more than 80% and no less than 20%, by weight, of algae in the algae-laden growing medium is extracted for harvesting.

13. The method of claim 10, further comprising:
receiving at least one of nutrients or alkali in the holding tray to facilitate cultivation of algae.

14. The method of claim 10, wherein the plurality of growing trays are positioned to cause cultivation of algae by extraction of atmospheric carbon dioxide by the algae.

* * * * *